United States Patent [19]

D'Amore et al.

[11] 4,052,332

[45] Oct. 4, 1977

[54] CATALYST REGENERATION WITH IMPREGNATION OF BISMUTH AND MOLYBDENUM

[75] Inventors: Michael Brian D'Amore, Wilmington, Del.; Arthur William Sleight, Kennett Square, Pa.

[73] Assignee: E. I. Du Pont de Nemours and Company, Wilmington, Del.

[21] Appl. No.: 678,708

[22] Filed: Apr. 20, 1976

[51] Int. Cl.$^2$ .................. B01J 23/92; C07C 121/02
[52] U.S. Cl. ................................ 252/413; 252/412; 260/465.3
[58] Field of Search ................. 252/412, 413; 260/465.3

[56] References Cited

U.S. PATENT DOCUMENTS

| 3,236,782 | 2/1966 | Koch | 252/411 R |
|---|---|---|---|
| 3,629,148 | 12/1971 | Dominik et al. | 252/413 |
| 3,746,657 | 7/1973 | Miller et al. | 252/437 |
| 3,766,092 | 10/1973 | Honda et al. | 252/437 |
| 3,882,159 | 5/1975 | Callahan et al. | 260/465.3 |
| 3,956,181 | 5/1976 | Grasselli et al. | 252/437 |
| B 260,945 | 1/1975 | Hausweiller et al. | 252/437 |

*Primary Examiner*—Patrick P. Garvin
*Assistant Examiner*—P. E. Konopka

[57] ABSTRACT

Process for regenerating a spent catalyst, which catalyst contains potassium, cobalt, nickel, iron, bismuth, phosphorus and molybdenum and sufficient oxygen to satisfy the valence of the other elements therein, on a support, e.g. silicon oxide, wherein at least a portion of the molybdenum has been lost during ammoxidation, comprising impregnating said catalyst with bismuth and molybdenum in solution so that at least some of the molybdenum lost is replaced, e.g., a typical impregnating solution is prepared by dissolving molybdenum trioxide and phosphoric acid in water, adding nitric acid and finally dissolving bismuth nitrate pentahydrate in the resultant solution.

14 Claims, No Drawings

CATALYST REGENERATION WITH IMPREGNATION OF BISMUTH AND MOLYBDENUM

BACKGROUND OF THE INVENTION

1. Field of the Invention

This invention relates to the regeneration of catalysts containing various metal oxides by impregnating the spent catalyst with a solution containing a combination of metals. More particularly, a catalyst for the production of acrylonitrile from propylene, ammonia and oxygen or air (ammoxidation) comprising the oxides of potassium, cobalt, nickel, iron, bismuth, phosphorus and molybdenum is regenerated by impregnating the spent catalyst with a solution comprising soluble molybdenum and bismuth species and thereafter calcining the treated catalyst to obtain an active catalyst.

2. Description of the Prior Art

It is known that certain molybdenum-containing catalysts which are especially adapted for ammoxidation tend to deactivate upon prolonged exposure to reactants at reaction conditions. It has also been observed that molybdenum is lost from the catalyst during reaction. In Dutch Pat. No. 7,411,063 it is suggested that one deactivation path is the loss of molybdenum and suggests the catalyst be reactivated in situ, i.e. without removal from the reactor, by contacting the ammoxidation catalyst with fluid-bed particles of molybdenum on an inert support. Optionally, the particles can contain other elements such as iron, bismuth or tellurium which may be useful in the regeneration, but particles consisting essentially of molybdenum on an inert support are preferred. The preferred method for preparing the particles involves spray drying an aqueous slurry containing the finely divided support material and finely divided molybdenum metal or molybdenum compound. An alternate preparation involves combining a solution of a molybdenum compound with a finely divided support material and thereafter drying and grinding the particles.

German Offenlegungschrift 2,352,196, published on Oct. 18, 1973, discloses a process for regenerating a catalytic matrix containing the oxides of cobalt and molybdenum, magnesium and molybdenum, nickel and molybdenum, manganese and molybdenum or mixtures thereof by impregnating the catalyst with a liquid containing compounds of bismuth, iron, tellurium or mixtures thereof that are at least partially soluble in the liquid and thereafter heating the impregnated matrix at an elevated temperature to form an active catalyst.

The regeneration of catalysts containing iron and molybdenum to restore lost molybdenum by impregnating the spent catalyst with a solution of an amine molybdate (a nonoxidizing compound of molybdenum), removing the solvent and further heating the catalyst is disclosed in U.S. Pat. No. 2,973,326, issued on Feb. 28, 1961.

The incorporation of iron into a spent bismuth phosphomolybdate catalyst to increase the activity thereof is disclosed in U.S. Pat. No. 3,629,148 issued on Dec. 21, 1971 and/or U.S. Application Ser. No. B260,945 published on Jan. 28, 1975.

SUMMARY OF THE INVENTION

A catalyst of the general formula $A_aB_bC_cFe_dBi_eMo_fO_x$ wherein A is at least one element selected from the group consisting of an alkali metal, rare earth metal, tantalum and niobium, B is at least one element selected from the class consisting of nickel and cobalt, C is at least one element selected from the class consisting of phosphorus and arsenic, wherein each subscript represents moles and "$a$" and "$c$" are numbers from 0 to 3, "$b$" is a number from 0.1 to 20, "$d$" is a number from 0.1 to 8, "$e$" is a number from 0.1 to 6, "$f$" is a number from 8 to 16, and "$x$" is a number determined by the valence requirements of the other elements present which catalyst is optionally on a support and is regenerated by intimately contacting said catalyst with molybdenum and bismuth in substantially aqueous solution, separating the catalyst thus contacted from any solution not absorbed by the catalyst and thereafter calcining the catalyst to form an active catalyst.

In a particular embodiment, the present invention involves a process for regenerating a catalyst initially comprising elements shown by the general formula $K_{(g)}Co_{(h)}Ni_{(i)}Fe_{(j)}Bi_{(k)}P_{(l)}Mo_{(m)}O_{(x)}$ wherein ($g$) through ($m$) represent moles and are numbers in the range 0.05–0.10, 4.0–5.0, 2.0–3.0, 2.5–3.5, 0.8–1.2, 0.1–1.0, 10.8–13.2 respectively, and wherein ($x$) is sufficient to satisfy the valence requirements of the other elements present, which comprises or consists essentially of impregnating the catalyst with an aqueous solution containing bismuth and molybdenum species in solution, e.g. a solution containing at least 29 grams/liter of molybdenum and 11 grams/liter of bismuth in solution until at least about 0.75 weight percent molybdenum and 0.28 weight percent bismuth, based upon the weight of catalyst or 1.5 and 0.56 weight percent, respectively, of the catalytic elements (ex support), is incorporated onto the surfaces of said catalyst, separating the catalyst thus treated from any solution not absorbed by the catalyst and thereafter calcining the resultant material to obtain a regenerated catalyst. In this manner at least about 50%, and preferably at least about 90% of the molybdenum which was lost from the catalyst during use is replaced, and the amount of bismuth in the catalyst is increased. The mole ratio of added molybdenum to bismuth is usually maintained in the range .5 to 20 and preferably 1 to 5.

In one preferred embodiment of the present invention either phosphorus or silicon is present in addition to bismuth and molybdenum in the treating solution. When phosphorus is present the solution can be prepared by dissolving sufficient molybdenum trioxide and phosphoric acid in water to provide a solution having at least 29 grams/liter of molybdenum and at least 0.8 gram/liter of phosphorus in solution, adding nitric acid and finally dissolving sufficient bismuth nitrate pentahydrate in the resultant solution to provide a solution having at least 11 grams/liter of bismuth.

DETAILED DESCRIPTION OF THE INVENTION

The regeneration process of the present invention may be applied to a wide variety of catalysts but is particularly adaptable to catalysts of the type described in U.S. Pat. Nos. 3,766,092 and 3,746,657 issued on Oct. 16, 1973 and July 17, 1973, respectively, and Dutch Pat. No. 7,114,722. The catalysts are generally described, as in the above indentified Dutch patent, by the general formula $A_aB_bC_cFe_dBi_eMo_fO_x$ wherein A is at least one element selected from the group consisting of an alkali metal, a rare earth metal, tantalum and niobium, B is one or more of the elements selected from the group consisting of nickel and cobalt, C is phosphorus or arsenic or both. The subscripts represent moles and "a" and "c" are numbers from 0 to 3, "b" is a number from 0.1 to 20, "d" is a number from 0.1 to 8, "e" is a number from 0.1 to 6, "f" is a number from 8 to 16, and "x" is a number determined by the valence requirements of the other elements present. The foregoing elements are usually on a silicon oxide support, which support comprises 40–60% by weight of the catalyst. These active catalysts are especially effective in powder form, e.g. powder having an average particle diameter of 50–70 microns and provide at least about 92% conversion of propylene with at least about 70% selectivity in ammoxidation of propylene to acrylonitrile. As used herein the term "conversion" is expressed as percent and is defined as the moles of propylene consumed divided by the moles of propylene fed multiplied by 100, and the term "selectivity" is expressed as percent and is defined as the moles of acrylonitrile produced divided by the moles of propylene consumed multiplied by 100. These parameters are determined by known analytical techniques, e.g. gas chromatography, using the ammoxidation apparatus and conditions described in Example 1. In a particular embodiment, these catalysts can be represented by the general formula $K_{(g)}Co_{(h)}Ni_{(i)}Fe_{(j)}Bi_{(k)}P_{(l)}Mo_{(m)}O_{(x)}$ wherein $(x)$ is a number determined by the valence requirements of the other elements present and wherein $(g)$ through $(m)$ are numbers in the range 0.05–0.10, 4.0–5.0, 2.0–3.0, 2.5–3.5, 0.8–1.2, 0.1–1.0, 10.8–13.2, respectively.

After prolonged exposure to reactants at reaction conditions, e.g. at conditions approximating those set forth in Example 1, as conditions for testing the effectiveness of the regeneration and including the variances experienced in commercial operation, the effectiveness of a catalyst decreases as evidenced by a decrease in conversion to about 90% or less and in selectivity to about 69% or less at which point it is dictated by economics that the catalyst be replaced. Catalysts which have decreased in effectiveness as described are termed "spent" and, generally, have lost from 0.4 to 1.2 moles of molybdenum, as expressed in the above general formula. However, the present invention can be applied to catalysts which exhibit a greater or lesser loss of activity and/or molybdenum than that discussed hereinabove. When a "spent" catalyst having substantially the general formula $K_{0.07}Co_{4.5}Ni_{2.5}Fe_3Bi_1P_{0.5}Mo_{11.25}O_x$ on a silicon oxide support wherein "x" is a number determined by the valence requirements of the other elements, which catalyst exhibits a conversion of 90% and a selectivity of 69%, is regenerated according to a preferred embodiment of the present process, the resultant catalyst contains the following elements substantially in the amounts indicated: $K_{0.07}Co_{4.5}Ni_{2.5}Fe_3Bi_{1.35}P_{.65}Mo_{12.7}O_x$ and when tested according to the procedures set forth in Example 1 demonstrates at least about 92% conversion and 75% selectivity.

It is critical to the present invention that a combination of bismuth and molybdenum be employed since satisfactory regeneration is not realized if only one metal is added to the catalyst. This requirement is unexpected since molybdenum is apparently the only metal which is lost from the catalyst. Bismuth and molybdenum may be simultaneously or sequentially contacted with the catalyst with simultaneous contact being preferred. Generally a Mo/Bi mole ratio in the range 0.5 to 20 in the impregnating solution can be employed but it is preferred to employ a ratio in the range of 1 to 5. In a preferred embodiment of the present invention, the Bi and Mo are present in a solution which contains one or more additional elements such as phosphorus or silicon preferably in the form of an oxyanion. The Bi, Mo and third element may be depicted as forming a chemical composition of the heteropolyacid class, e.g., an acid containing oxygen, molybdenum, phosphorus, and/or silicon and bismuth. Alternatively, a chemical composition may be depicted as a bismuth salt of a heteropolyacid which includes the Mo and one or more other elements. Other representations of the chemical composition should be apparent to those skilled in the art. Other catalyst elements such as iron and antimony, etc. can be present in the impregnating solution without departing from the spirit of the present invention. These additional elements can be associated with and/or an integral portion of the heteropolyacid or salt.

The compounds which are used to regenerate the catalyst are most efficiently handled in solution. The solutions may be aqueous, organic or combinations of the foregoing, depending upon the form of bismuth and molybdenum employed. Aqueous or substantially aqueous solutions i.e. those solutions wherein water is the predominant solvent are preferred. The following discussion is principally directed to aqueous solutions, it being understood that other functionally equivalent systems, e.g. vapor phase systems, wherein the elements are in a form such that they are readily accessible to the catalyst surfaces are within the purview of the present invention.

In an aqueous system molybdenum can be obtained from a variety of sources. Illustrative are molybdic acid, soluble alkali, alkali metal, ammonium or organic amine molybdates such as sodium, potassium, lithium, calcium, barium, magnesium, ammonium and methylamine molybdates. Molybdenum compounds such as molybdenum oxybromide, molybdenum oxychloride, molybdenum hexafluoride, molybdenum oxyfluoride, molybdenum triphenyl, molybdenum hexacarbonyl and molybdenum sulfide which can be hydrolyzed and/or oxidized in the presence of water to yield an oxide of molybdenum can be used. In cases where phosphorus is also present, the molybdenum compound may react to form a phosphomolybdate. Molybdenum trioxide is the preferred source of molybdenum. Phosphoric acid is the preferred source of phosphorus but compounds such as phosphorus pentoxide, phosphorus trioxide, hypophosphoric acid, metaphosphoric acid, phosphorus pentachloride, phosphorus pentabromide, phosphorus oxychloride, phosphorus oxybromide, trimethylphosphate and triphenylphosphate which can form an aqueous solution of phosphoric acid can also be employed. Phosphorus and molybdenum can be supplied when both are present by soluble ammonium, alkali or alkaline earth metal phosphomolybdates such as phosphomolybdic acid, sodium phosphomolybadate and potassium phosphomolydate.

It may be desirable to optimize the impregnation by dealing only with solutions and if the source of molybdenum and/or phosphorus is not completely soluble, i.e. produces a slurry, the solids are preferably removed by filtration before the next step in the preparation of the impregnating solution. As should be obvious to one skilled in the art in view of the foregoing, in order to maximize solubility of Bi and Mo compounds or to permit complete solution, it may be advantageous to maintain the solution either basic, neutral or acidic depending upon the compounds employed. When molybdenum trioxide and phosphoric acid in aqueous solution are employed it is preferred to maintain the solution acidic to maximize solubility.

Preferably the bismuth compound should be soluble in the impregnating solution. In addition to bismuth nitrate which is the preferred source of bismuth in the aqueous system, compounds soluble in aqueous nitric acid such as bismuth trioxide, bismuth hydroxide, bismuth oxychloride, bismuth subnitrate, bismuth sulfide, bismuth oxalate and bismuth tartrate which can hydrolyze in the molybdenum and/or phosphomolybdenum solution can be employed.

In cases where silicon is present, the silicon is conveniently supplied as silicomolybdic acid but soluble ammonium and alkali metal silicon compounds such as orthosilicic acid, sodium silicate and potassium silicate as well as organosilicates such as ethyl orthosilicate may be used.

In some cases, the molybdenum, phosphorus, bismuth or silicon compound chosen will introduce undesirable amounts of ions such as sulfide and chloride in the impregnating solution. However, such ions are readily removed at any step in the preparation of the impregnating solution by methods well known in the art, e.g. treatment with adsorbents such as zeolites, molecular sieves or ion exchange resins.

Since it is desirable to avoid or at least minimize solids in the impregnating solution it may be necessary to adhere to a prescribed sequence of addition to prevent reactions which form precipitates. In an aqueous system it is generally preferred to place the molybdenum and optionally phosphorus, in solution, to acidify, e.g. by the addition of 5–60% and preferably 5–30% by volume of the impregnating solution of 15.4N nitric acid, to cool the acidified solution and then to dissolve the bismuth compound. Likewise, it may be advantageous to heat the solution to increase the rate at which the compounds dissolve; however, elevated temperatures can cause precipitation in which circumstances it is desirable to cool the solution. For example, when the impregnating solution for a typical "spent" catalyst is prepared by adding molybdenum trioxide and phosphoric acid to water, heating to accelerate the solution process and thereafter acidifying the solution by adding nitric acid, it is preferable to cool the solution to less than about 85° C and more preferably to a temperature in the range 20°–30° C before addition of the bismuth nitrate in order to prevent precipitation.

The concentration of impregnants in the solution is proportional to the amount of impregnant incorporated onto the surfaces of the catalyst. For effective regeneration it is necessary to add at least 0.75 weight percent molybdenum, 0.28 weight percent bismuth and optionally 0.02 weight percent phosphorus and/or silicon, all based upon the weight of the catalyst to the specific spent catalysts described above. If it is desired to incorporate the foregoing minimum amounts of elements in one contact of the catalyst and impregnating the solution, the solution must contain at least 29 grams/liter of molybdenum, 11 grams/liter of bismuth and, optionally, 0.8 grams/liter of phosphorus and/or silicon. If multiple contact of catalyst and impregnating solution is practiced the concentration of the components in the solution may be reduced in proportion to the number of contacts without departing from the spirit of the present invention.

The impregnating solution may be contacted with the catalyst by several methods including drip or spray impregnation and filtration immpregnation. Drip or spray impregnation, as the names imply, involve tumbling the catalyst while metering impregnating solution thereon. The volume of solution employed in the drip or spray impregnation should preferably be not greater than 110% of the pore volume of the catalyst for optimum results. A substantial excess of impregnating solution is contacted with the catalyst in the preferred filtration impregnation and the excess is removed before the catalyst is calcined. Many effective impregnating solutions, e.g. those having a high acid content, can react with the catalyst and cause dissolution and/or rearrangement of the catalyst, which reactions can adversely affect catalyst efficiency. Therefore, it is preferred, especially in filtration impregnation, to contact the catalyst with an impregnating solution which will rapidly introduce the desired level of elements to the catalyst and after contact to rapidly separate the catalyst from any excess impregnating solution.

The impregnated catalyst must be dried and calcined regardless of the method of impregnation to provide an active catalyst. Drying may be accomplished by any convenient means known to those skilled in the art, e.g. by heating at 25°–125° C for 24–48 hours or concurrently with calcination. Calcination is conveniently accomplished by heating the catalyst to a temperature in the range 300°–700° C and preferably in the range 450°–650° C in an oxidizing atmosphere, preferably at a temperature of 500° C for a period of about 1 hour.

EXAMPLE 1

A solution is prepared by combining 16.40 g molybdenum trioxide, 1.31 g phosphoric acid (85%) and 300 ml water in a 500 ml glass flask and boiling the mixture with periodic addition of water to maintain a volume of 250 ml until a solution is obtained (about 6 hours). Water then is evaporated until the solution volume is 104 ml following which the flask and its contents are cooled to about 25° C and 10 ml of nitric acid (70%) is added. The contents of the flask are stirred and 14.53 g bismuth nitrate pentahydrate are added. Stirring is continued until the bismuth nitrate is dissolved.

The spent catalyst is in powder form and on a silicon oxide support which support amounts to about 50% by weight of the catalyst. The catalyst has an average particle size of about 66 microns, a pore volume of 0.25 cc per gram and a composition of about $K_{0.07}Co_{4.5}Ni_{2.5}Bi_{1.0}P_{0.5}Mo_{11.25}O_x$ wherein "x" is a number determined by the valence requirements of the other elements present. Approximately 450 g of this spent catalyst is placed in a 1-gallon stainless steel beaker having internal mixing fins. The beaker is placed on a rolling device and rotated at about 30 rpm at about a 30° angle from the horizontal while the solution prepared as described above is dripped onto the spent catalyst following which the treated catalyst is dried at 115° C than calcined by heating to about 500° C over a period of 1 hour and held at that temperature for an additional hour. The resultant catalyst has a composition of about $K_{0.07}Co_{4.5}Ni_{2.5}Fe_{3.0}Bi_{1.35}P_{0.65}Mo_{12.7}O_x$ and contains 1.39 weight percent added Bi, 0.08 weight percent added P and 2.43 weight percent added Mo.

Approximately 400 grams of the catalyst as set forth above was charged to a 3-inch diameter fluidized bed reactor. Ammonia, propylene and air premixed at mole ratio 1.09/1.0/10.1 at a temperature of 440° C and a pressure of 12 psig was passed upwardly through the catalyst at a gas velocity of 1.74 cm/sec to fluidize the bed. The conversion of propylene was 92% and selectivity to acrylonitrile was 76% as compared to a 90% conversion and 69% selectivity for the spent catalyst tested in the same manner.

EXAMPLES 2-13

Samples of spent catalyst having a composition and condition substantially the same as the spent catalyst of Example 1 are regenerated in accordance with Example 1 except that (1) the amounts of Bi, P and Mo added to the spent catalyst are varied as indicated and (2) the amounts of impregnants are increased to provide a final impregnation solution volume of 250 ml which is sufficient to permit filtration impregnation. For convenience in handling, the solution is divided into two 125-ml portions. Each portion is contacted with 225-gram portions of spent catalyst and excess impregnating solution is promptly removed by filtration before the impregnated catalyst is dried, calcined and tested. The results are given in the Table. An excess of $MoO_3$, $H_3PO_4$ and $Bi(NO_3)_3.5H_2O$ (as calculated from the measured pore volume of the catalyst) is added to insure saturation of the pores.

In the Table the weight percent of elemental impregnant incorporated into the spent catalyst is calculated from the measured pore volume. The calculated value for added molybdenum corresponds closely to the amount determined by analysis but a greater variance exists between the calculated and analyzed values for bismuth because of analytical problems. However, it is not necessary to rely upon analytical results to determine the amount of elements added to the catalyst. For example, if the impregnating solution is contacted with the catalyst by drip or spray impregnation practically all of the compounds in a given solution are placed on the catalyst because no solution is removed. Since the amount of compounds used to prepare the solution are known, the amounts on the catalyst can be determined by simple calculation. In addition, it is known that molybdenum, bismuth and/or phosphorus or silicon are not preferentially absorbed during impregnation, therefore the amount of elements added to the catalyst will be in practically the same ratio as in the impregnating solution. Thus, one may analyze for the amount of molybdenum added and then calculate the amounts of other elements added in either drip or filtration impregnation. An analysis of the amount and composition of any impregnating solution removed from the catalyst during filtration impregnation can also be used to determine the amount of added elements.

EXAMPLES 14-17

The impregnation procedure of Examples 1-13 was modified by sequentially contacting 450 grams of the catalyst with solutions containing molybdenum and bismuth. The molybdenum was introduced as ammonium heptamolybdate (as 100% $(NH_4)_6Mo_7O_{24}.4H_2O$) in 115 ml of an aqueous solution in the amounts indicated in the Table. The bismuth was introduced as bismuth nitrate (as 100% $Bi(NO_3)_3.5H_2O$) in 115 ml of an aqueous solution containing the amounts of bismuth nitrate indicated in the Table. The solutions were contacted with the catalyst by drip impregnation according to the general procedure of Example 1. The molybdenum was added before the bismuth in Examples 14 and 15 and after the bismuth in Examples 16 and 17. The catalyst was dried and calcined before and after the addition of the bismuth in Example 14 but only dried before the addition of bismuth in Example 15. The same variance in calcining and/or drying was employed in Examples 16 and 17. The regenerated catalyst was tested as in Example 1 and the results are reported in the Table.

EXAMPLE 18

Example 1 was repeated except that the phosphoric acid was replaced with 2.70 grams of sodium silicate ($Na_2SiO_3.9H_2O$) to incorporate 0.06 weight percent silicon and 0.097 weight percent sodium in addition to the elements shown in the Table.

EXAMPLE 19

Example 1 was repeated except that 1.62 grams of sodium nitrate was added along with the bismuth nitrate to incorporate 0.097 weight percent sodium into the catalyst in addition to the elements shown in the Table.

CONTROLS A-D

Example 1 was repeated except that solutions containing molybdenum or bismuth alone and molybdenum and phosphorus alone were employed to impregnate the catalyst. The results are shown in the Table.

The foregoing examples and controls clearly demonstrate that molybdenum or bismuth alone will not provide satisfactory regeneration and that a combination of the foregoing elements is necessary for optimum results.

TABLE

| Example No. | Amount of Impregnant in 250 ml of Solution (gms) | | | Elemental Impregnant Incorporated in Catalyst (Weight %) | | | Catalyst Performance | |
|---|---|---|---|---|---|---|---|---|
| | $MoO_3$ | $H_3PO_4$ | $Bi(NO_3)_3.5H_2O$ | Bi | P | Mo | Conversion of Propylene (%) | Selectivity of Acrylonitrile (%) |
| 2 | 27.60 | 4.14 | 11.62 | 0.56 | 0.12 | 2.05 | 94 | 72 |
| 3 | 38.80 | 5.82 | 52.29 | 2.51 | 0.17 | 2.87 | 92 | 75 |
| 4 | 10.40 | 1.56 | 17.43 | 0.84 | 0.048 | 0.77 | 98 | 70 |
| 5 | 27.0 | 4.06 | 52.29 | 2.51 | 0.12 | 2.00 | 94 | 75 |
| 6 | 26.0 | 3.91 | 23.24 | 1.11 | 0.12 | 1.92 | 94 | 74 |
| 7 | 27.6 | 4.14 | 5.81 | 0.28 | 0.12 | 2.05 | 94 | 71 |
| 8 | 38.0 | 5.71 | 29.05 | 1.39 | 0.17 | 2.82 | 93 | 73 |
| 9 | 10.34 | 0.83 | 5.81 | 0.28 | 0.025 | 0.77 | 95 | 71.6 |
| 10[a] | 6.3 | .50 | 2.90 | 0.28 | 0.02 | 0.81 | 95.1 | 70 |
| 11[b] | 37.28 | 0 | 29.06 | 1.39 | 0.06 | 2.43 | 92.8 | 76.7 |
| 12[c][d] | 20.11 | 0 | 14.53 | 1.39 | 0 | 2.43 | 94.9 | 70.0 |
| 13[c][e] | 6.38 | 0 | 5.85 | 0.56 | 0 | 0.77 | 96 | 71.4 |
| 14 | 20.11 | 0 | 14.53 | 1.39 | 0 | 2.43 | 93.1 | 73.8 |
| 15 | 20.11 | 0 | 14.53 | 1.39 | 0 | 2.43 | 94.9 | 74.3 |
| 16 | 20.11 | 0 | 14.53 | 1.39 | 0 | 2.43 | 94.0 | 70.0 |
| 17 | 20.11 | 0 | 14.53 | 1.39 | 0 | 2.43 | 93.7 | 74.1 |
| 18 | 16.40 | — | 14.53 | 1.39 | 0 | 2.43 | 91 | 76.3 |
| 19 | 16.40 | 1.31 | 14.53 | 1.39 | .08 | 2.43 | 90 | 76 |
| Control | | | | | | | | |

TABLE-continued

| Example No. | Amount of Impregnant in 250 ml of Solution (gms) | | | Elemental Impregnant Incorporated in Catalyst (Weight %) | | | Catalyst Performance | |
|---|---|---|---|---|---|---|---|---|
| | MoO$_3$ | H$_3$PO$_4$ | Bi(NO$_3$)$_3$ · 5H$_2$O | Bi | P | Mo | Conversion of Propylene (%) | Selectivity of Acrylonitrile (%) |
| A | 0 | 0 | 14.53 | 1.39 | 0 | 0 | 86 | 60 |
| B | 27.0 | 4.06 | 0 | 0 | 0.12 | 2.00 | 90.4 | 69 |
| C(f) | 16.28 | 0 | 0 | 0 | 0 | 1.78 | 90.7 | 68.3 |
| D | 20.11 | 0 | 0 | 0 | 0 | 2.43 | 89 | 69.7 |

(a)Amount of impregnant in 115 ml of solution added to 450 grams of catalyst by drip impregnation according to the general procedure of Example 1.
(b)Approximately 37.28 grams of molybdosilicic acid (H$_4$SiMo$_{12}$O$_{40}$ · 7H$_2$O as 100%) in 250 ml of water was employed in place of the molybdenum oxide and phosphoric acid.
(c)Molybdenum added expressed as grams of ammonium heptamolybdate (as 100% NH$_4$Mo$_7$O$_{24}$4H$_2$O) in 115 ml of solution added by drip impregnation to 450 grams of catalyst according to the general procedure of Example 1.
(d)Nitric acid added to the impregnating solution to produce a concentration of 6.2N.
(e)Nitric acid added to the impregnating solution to produce a concentration of 1.6N.
(f)Approximately 105 ml of solution were employed.

We claim:

1. A process for regenerating a catalyst of the general formula A$_a$B$_b$C$_c$Fe$_d$Bi$_e$Mo$_f$O$_x$ wherein A is at least one element selected from the group consisting of an alkali metal, rare earth metal, tantalum and niobium, B is at least one element selected from the class consisting of nickel and cobalt, C is at least one element selected from the class consisting of phosphorus and arsenic, "a" and "c" are numbers from 0 to 3, "b" is a number from 0.1 to 20, "d" is a number from 0.1 to 8, "e" is a number from 0.1 to 6, "f" is a number from 8 to 16, and "x" is a number determined by the valence requirements of the other elements present, wherein said catalyst has become at least partially deactivated by exposure to ammoxidation conditions which exposure is accompanied by the loss of a portion of the molybdenum originally present in the catalyst, which process comprises impregnating said catalyst with molybdenum and bismuth, separating the catalyst thus impregnated from any bismuth and molybdenum not absorbed by the catalyst and thereafter calcining the catalyst by heating the catalyst to a temperature in the range of about 300°-700° C in an oxidizing atmosphere to form a regenerated catalyst wherein the mole ratio of added molybdenum to bismuth is in the range 0.5-20 and at least 50% of the molydbenum lost is replaced.

2. The process of claim 1 wherein the molybdenum and bismuth are present in substantially aqueous solution.

3. The process of claim 2 wherein said molybdenum and bismuth are present in the same solution.

4. The process of claim 3 wherein an element selected from the class consisting of phosphorus, silicon and mixtures thereof are present in the solution.

5. A process for the regeneration of a spent ammoxidation catalyst consisting essentially of potassium, cobalt, nickel, iron, bismuth, phosphorus and molybdenum and sufficient oxygen to satisfy the valences of the other elements therein, on a support wherein said catalyst has become at least partially deactivated by exposure to ammoxidation conditions which exposure is accompanied by a loss of molybdenum from the catalyst which process comprises impregnating said catalyst with bismuth and molybdenum in substantially aqueous solution and wherein the mole ratio of added molybdenum to bismuth is maintained in the range 0.5 to 20, until at least 50% of the molybdenum lost is replaced separating the catalyst thus treated from any solution not absorbed on the catalyst and thereafter calcining the catalyst by heating the catalyst to a temperature in the range of about 300°-700° C in an oxidizing atmosphere to obtain a regenerated catalyst.

6. The process of claim 5 wherein an element selected from the class consisting of phosphorus, silicon and mixtures thereof are added to the catalyst in addition to molybdenum and bismuth at a mole ratio of added molybdenum to said element in the range 2 to 15.

7. The process of claim 5, wherein the molybdenum and bismuth are present in the same substantially aqueous solution.

8. A process for regenerating an ammoxidation catalyst initially having the general formula K$_{(g)}$Co$_{(h)}$Ni$_{(i)}$Fe$_{(j)}$Bi$_{(k)}$P$_{(l)}$Mo$_{(m)}$O$_{(x)}$ wherein (g) through (m) are numbers in the range of 0.05-0.10, 4.0-5.0, 2.0-3.0, 2.5-3.5, 0.8-1.2, 0.1-1.0, 10.8-13.2, respectively, and wherein (x) is sufficient to satisfy the valence requirements of the other elements present and wherein said catalyst has lost from about 0.4 to about 1.2 moles of molybdenum as expressed in the above formula by exposure to ammoxidation, which comprises impregnating said catalyst with an aqueous solution comprising bismuth and molybdenum species until at least about 1.5 weight percent molybdenum and 0.56 weight percent bismuth, based upon the weight of the catalytic elements, is incorporated onto the surfaces of said catalyst, separating the catalyst thus treated from any solution not absorbed by the catalyst and thereafter calcining the catalyst by heating the catalyst to a temperature in the range of about 300°-700° C in an oxidizing atmosphere to obtain a regenerated catalyst.

9. The process of claim 8 wherein said aqueous solution contains a third species selected from the class consisting of phosphorus, silicon and mixtures thereof and wherein at least 0.02% by weight based upon the weight of catalyst of said third species is also incorporated onto the catalyst.

10. The process of claim 8 wherein the said solution prepared by dissolving molybdenum trioxide and phosphoric acid in water, adding 5-60% by volume based upon the volume of the water of nitric acid as 15.4N nitric acid and finally dissolving bismuth nitrate pentahydrate in the resultant solution.

11. The process of claim 8 wherein the solution contains at least 29 grams/liter of molybdenum and at least 11 grams/liter of bismuth.

12. The process of claim 11, wherein the solution contains at least 0.8 grams/liter of phosphorus.

13. A process for regenerating an ammoxidation catalyst which catalyst comprises the combined oxides of potassium, cobalt, nickel, iron, bismuth, phosphorus and molybdenum on a silicon oxide support and in powder form, wherein said catalyst has become at least partially deactivated by exposure to ammoxidation conditions said process comprising thoroughly contacting said catalyst with a solution prepared by dissolving sufficient molybdenum trioxide and phosphoric acid in water to provide a solution having at least 29 grams/liter of molybdenum and at least 0.8 gram/liter of phosphorus, adding nitric acid and finally dissolving sufficient bismuth nitrate pentahydrate in the resultant solution to provide a solution having at least 11 grams/liter of bismuth, separating the catalyst from any solution not absorbed therein and calcining the catalyst thus treated at a temperature in the range 450°–650° C in an oxidizing atmosphere to form an active catalyst.

14. The process of claim 13 wherein 5–60% by volume of 15.4N nitric acid is added to said solution.

* * * * *